US012133941B2

(12) United States Patent
McMillan

(10) Patent No.: US 12,133,941 B2
(45) Date of Patent: Nov. 5, 2024

(54) UV-C UPPER AIR PURIFIER WITH DOWN LIGHTING COMBINED FIXTURE

(71) Applicant: George Erik McMillan, Hickory, NC (US)

(72) Inventor: George Erik McMillan, Hickory, NC (US)

(*) Notice: Subject to any disclaimer, the term of this patent is extended or adjusted under 35 U.S.C. 154(b) by 0 days.

(21) Appl. No.: 18/447,554

(22) Filed: Aug. 10, 2023

(65) Prior Publication Data

US 2023/0381365 A1 Nov. 30, 2023

Related U.S. Application Data

(63) Continuation of application No. 17/711,962, filed on Apr. 1, 2022, now Pat. No. 11,724,000.

(60) Provisional application No. 63/169,867, filed on Apr. 1, 2021.

(51) Int. Cl.

| | |
|---|---|
| ***A61L 9/20*** | (2006.01) |
| ***F21S 8/06*** | (2006.01) |
| ***F21V 33/00*** | (2006.01) |
| ***G01V 8/20*** | (2006.01) |
| *F21Y 115/10* | (2016.01) |

(52) U.S. Cl.

CPC . *A61L 9/20* (2013.01); *F21S 8/06* (2013.01); *F21V 33/0096* (2013.01); *G01V 8/20* (2013.01); *A61L 2209/111* (2013.01); *A61L 2209/12* (2013.01); *A61L 2209/15* (2013.01); *F21Y 2115/10* (2016.08)

(58) Field of Classification Search

CPC .......... A61L 9/20; F21S 8/06; F21V 33/0096; G01V 8/20

See application file for complete search history.

(56) References Cited

U.S. PATENT DOCUMENTS

| | | | | |
|---|---|---|---|---|
| 10,894,104 | B1 * | 1/2021 | Kim | A61L 9/20 |
| 11,305,031 | B2 * | 4/2022 | Sood | A61L 9/22 |
| 2021/0353813 | A1 * | 11/2021 | Wald | A61L 9/20 |
| 2022/0241444 | A1 * | 8/2022 | Igarashi | A61L 2/10 |
| 2022/0265889 | A1 * | 8/2022 | Bergenek | F21S 8/061 |
| 2022/0288253 | A1 * | 9/2022 | Yahnke | F21S 8/026 |
| 2022/0296764 | A1 * | 9/2022 | Roe | A61L 2/24 |
| 2023/0001029 | A1 * | 1/2023 | Barron | A61L 9/20 |
| 2023/0039310 | A1 * | 2/2023 | Baarman | A61L 9/20 |
| 2023/0061757 | A1 * | 3/2023 | Smithson | A61L 2/10 |

* cited by examiner

*Primary Examiner* — Christopher E Dunay

(74) *Attorney, Agent, or Firm* — Lambert Shortell & Connaughton; David J. Connaughton, Jr.

(57) ABSTRACT

An air purifying light system using unsafe UV-C emitters mounted on an upward facing portion of the frame of the system and at least visible light LEDs mounted on a lower facing portion of the frame, wherein the UV-C emitters are configured to kill viruses and pathogens in a sanitization zone formed between the frame and the ceiling.

13 Claims, 4 Drawing Sheets

200

UV-C UPPER AIR PURIFIER WITH DOWN LIGHTING COMBINED FIXTURE

RELATED APPLICATIONS

This application claims the benefit of U.S. Provisional Patent Application No. 63/169,867 filed on Apr. 1, 2021; which is herein incorporated by reference in entirety.

TECHNICAL FIELD

The present invention generally relates to ceiling light fixtures, and particularly to light fixtures that are configured to sterilize or purify the surrounding air.

BACKGROUND

Inside buildings, medical facilities and schools it is desirable and sometimes even necessary, to eradicate germs, viruses, and microbes from the air and surfaces of rooms. With the fear of new strains of viruses and other pathogens it is found that UV-C has the ability to quickly inactivate such microorganisms. Current systems utilize UV-C emitters by drawing air into a small internal area where the drawn in air is exposed to UV-C emissions. The present application and embodiments are to improve upon previous systems while providing a more integrated approach into lighting that can provide broader sanitization and purification to a given room. These and other advantages will become apparent to those skilled in the art upon reviewing the descriptions and drawings provided herewith.

SUMMARY

In one embodiment, an air purifying light system includes a frame having an upper facing portion and lower facing portion that is attached to a suspension system that is configured to suspend the frame from below the ceiling. A plurality of visible light emitting LED's are positioned on the lower facing portion of the frame to direct visible light below the frame. The upper facing portion of the frame includes a plurality of UV-C emitters in the range of 235-280 nm positioned to emit upward towards the ceiling. This space between the frame and the ceiling becomes a sanitizing or purifying zone, as the 235-280 nm emissions are configured to kill viruses, pathogens, bacteria and other microbes, thus sterilizing the air above the frame.

In a variation to the above embodiment, the air purifying light system, can also include a plurality of UV-C emitters in the range of 200-235 nm positioned on the lower facing portion of the frame, which have currently been determined are not harmful to living beings, such as humans, when exposed. However, these wavelengths are still effective at neutralizing viruses, pathogens, bacteria and other microbes, albeit they take more time to be effective as compared to the 235-280 nm range.

In yet another variation, the air purifying light system can include one or more sensors positioned to form an invisible barrier shield at or just below the level of the frame. These one or more sensors can be in communication with a controller that is configured to turn off the UV-C emitters in the 235-280 nm range positioned on the upward facing portion of the frame once an object is detected that passes through or interrupts the barrier.

The suspension system can be configured to suspend the frame at least 1 foot below the ceiling, at least 2 feet below the ceiling and at least 4 feet below the ceiling.

In yet another variation of the above embodiment, he air purifying light system can include an air circulation system that causes air below the frame to circulate with the air above the frame or the sanitization/purification zone. The air circulating system can include one or more ceiling fans. These one or more ceiling fans can be independently mounted or directly connected to the frame.

Alternative or in addition to the barrier, the air purifying light system can include an occupancy sensor(s) that is connected to a controller that operates the UV-C emitters. In such a scenario, the air purifying light system could be configured to include UV-C emitters in the range of 235-280 nm position on the lower facing portion of the frame, which are only activated once the occupancy sensors determine that the room or area is empty. Thus, ensuring a safe environment for using the UV-C emitters in the range of 235-280 nm.

In some variations to the above embodiment, the UV-C emitters installed on the lower portion lower facing portion of the frame are going to be either 222 nm or 233 nm wavelength emitters.

In some variations to the above embodiment, the UV-C emitters installed on the upper facing portion of the frame are either 254 nm, 270 nm or 272 nm wavelength emitters.

In some variations to the above embodiment, the air purifying light system frame is composed of an outer perimeter and an inner perimeter, having an aperture formed about the inner perimeter.

In other variations, T the ceiling is devoid of any material that can reflect greater than 5% of the light generated by the UV-C emitter in the range of 235-280 nm on the upward facing portion.

In another embodiment, an air purifying light system includes: a frame having an upper facing portion and a lower facing portion; a suspension system that is configured to suspend the frame from the ceiling; a plurality of visible light emitting LED's positioned on the lower facing portion of the frame, to direct visible light below; a plurality of UV-C emitters in the range of 200-235 positioned on the lower facing surface that are configured to kill viruses and pathogens while being safe to operate with humans in the vicinity, thus sterilizing the air below the frame; a a plurality of UV-C emitters in the range of 235-280 nm positioned on the upward facing surface, which are configured to kill viruses and pathogens, thus sterilizing the air above the frame.

This alternative air purifying light system further includes one or more barrier sensors configured to determine in an invisible barrier formed at the position of the frame has been breached, whereupon a breach, a controller can receive the signals from the one or more barrier sensors and turn off power to the plurality of UV-C emitter in the range of 235-280 nm positioned on the upward facing surface.

The alternative air purifying light system can also include an air circulating system that causes air below to circulate with air above the frame.

Additional detailed description of the above embodiments is provided below.

DETAILED DESCRIPTION

As noted above one of the purposes of the present embodiments is to provide an integrated UV-C air purification light system to both provide light to a given area, while sterilizing the air and surfaces in that given area. It is well understood that UV-C emissions in the range of 200-280 nm are effective at killing viruses, pathogens, bacteria, and microbes. However, it has currently been determined that UV-C in the range of 235 nm to 280 nm can be dangerous to living things, thus it should not be used when living beings (people and animals) are within the area being treated or exposed to UV-C emissions in this 235-280 nm range. For this description this will be considered the 'unsafe' UV-C emission range. As a result of these unsafe UV-C emitters, previous systems have attempted to completely enclose or encase the emissions into a confined area, so as to ensure safety.

It should also be understood that recent testing has confirmed that UV-C emissions in the range of 200-235 nm are generally safe to use around living beings, such as humans and animals, while still being effective at neutralizing viruses and so forth. Although UV-C emitters in the 200-235 nm are effective, in some analysis it has been determined that UV-C in the 235-280 can be 6-8 times more effective, which substantially increases the purification rate of a given volume or space. Again, for purposes of this description safe UV-C emissions will be in the range of 200-235 nm. If additional analysis is provided from the scientific community that shifts these ranges up or down some, it should be noted that the principle being provided is to have strategically positioned and controlled in the systems described herein 'unsafe' UV-C emitters and 'safe' UV-C emitters. Generally, the unsafe UV-C emitters are operating or positioned to expose areas devoid of living beings, while the safe UV-C emitters can be included to operate in the same space as living beings.

One of the advantages of the embodiments and methods described herein are the ability to effect large areas of volume, without the need of complex circulating systems or enclosures, at the same time providing a lighting system to the area or room where the systems and methods are being applied.

Figure 1A:
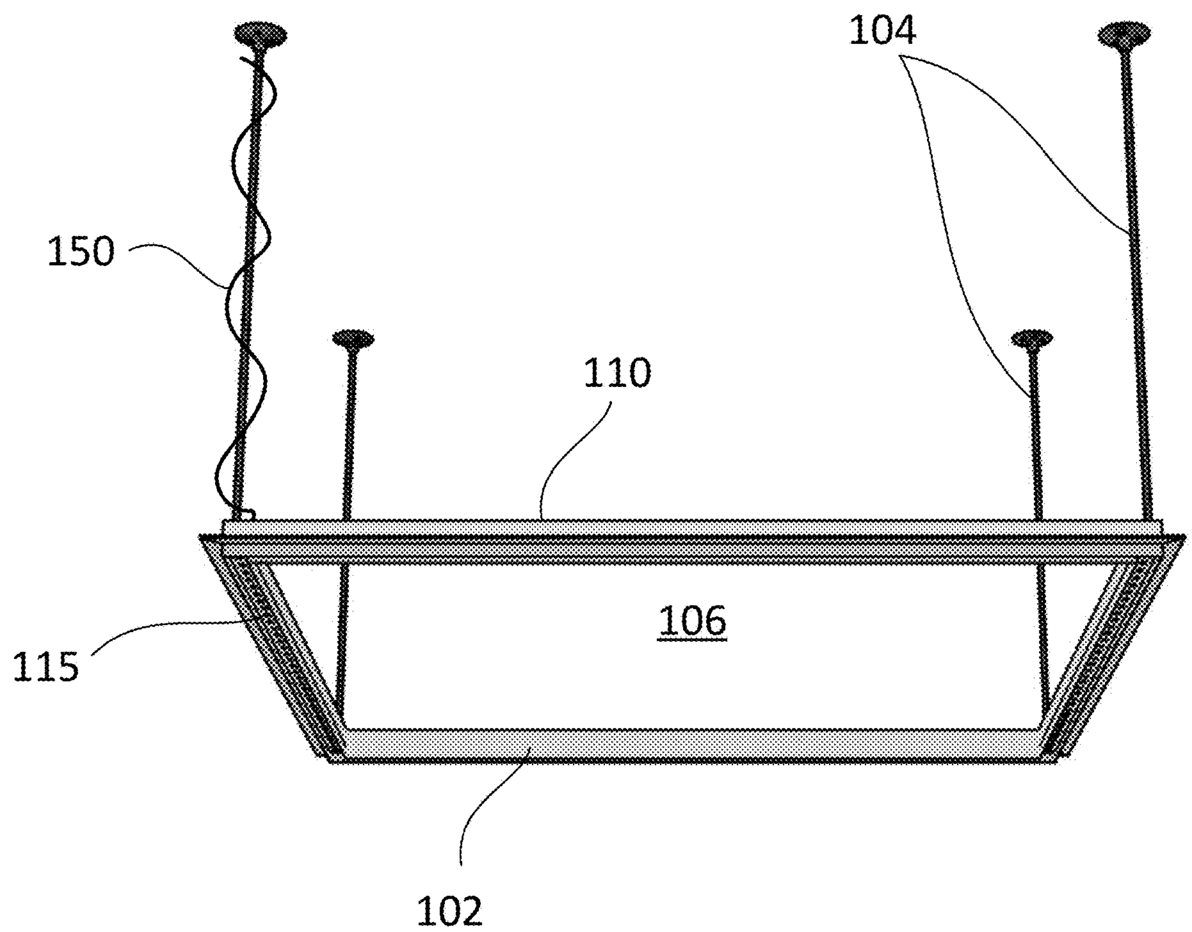
FIG. 1A is an illustration of a perspective view of an air purifying light system.

For example, now turning to FIG. 1A, which includes a perspective view of an air purifying light system 100A that includes a frame 102 that has lower-facing and upward facing portions and is suspended by a suspension system 104. The suspension system can include one or more rods, chains or other similar mechanical fixtures designed to be affixed to the ceiling or structure of the ceiling on one end and the frame on the other end. A power supply 150 can connect to and provide power, and some instances can include additional control circuits, to the LED lights 115 that are configured to emit visible light and mounted on the lower facing portion of the frame, thus emitting light downward into the room or area it is being hung. On the upper facing portion of the frame 102 are mounted 'unsafe' UV-C emitters in the 235-280 nm range. These unsafe emissions are directed upwards and, in a space, or volume disposed between the frame and the ceiling. This above the frame volume (or sanitization zone) is generally devoid of living beings. Air can freely circulate above and below the frame 102 with or without active circulating systems, as the movement of individuals below, the heat generated by the LEDs and other normal occurring events cause the air to circulate. This circulation can be aided by air circulating systems as will be discussed further below. This 100A system can also include an aperture, which can allow for maximum air circulation above and below the frame, thus eliminating stagnant zones or areas where air gets trapped.

Figure 1B:
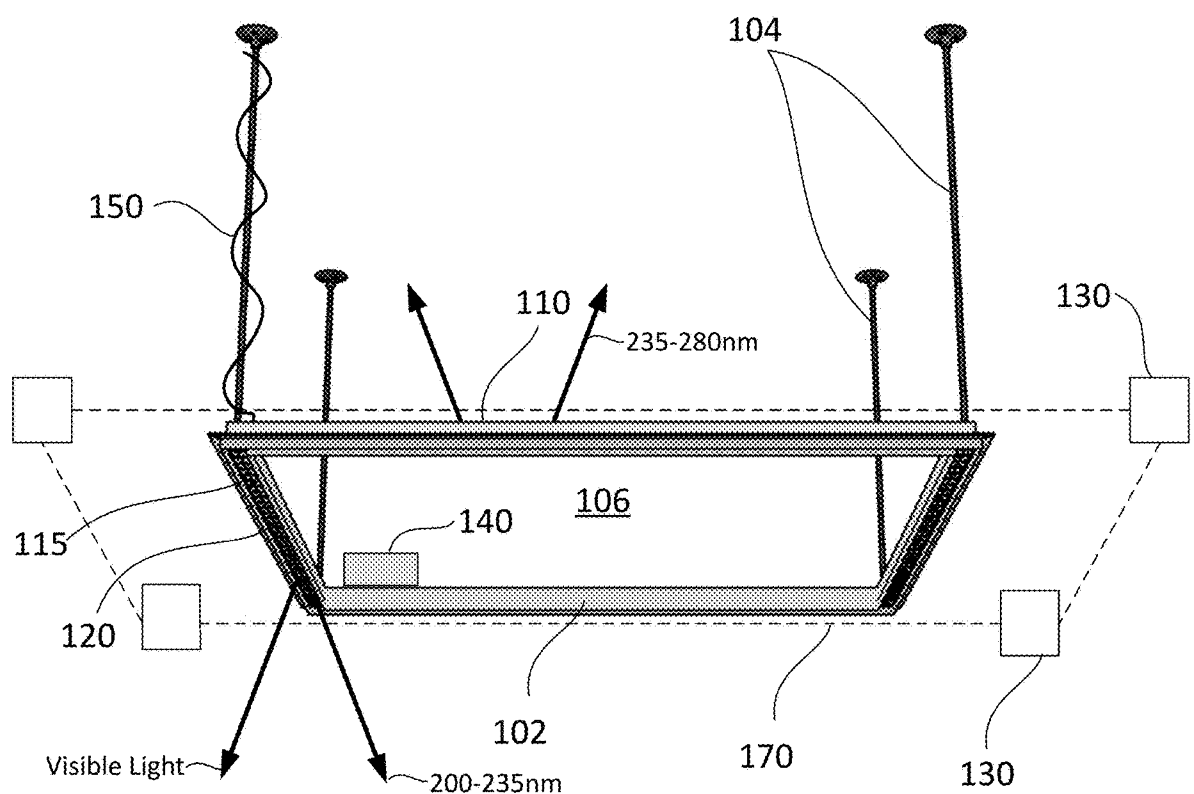
FIG. 1B is an illustration of an alternative air purifying light system that includes UV-C emitters on the upper and lower frame portions.

Now referring to FIG. 1B, an alternative air purifying light system 100B also includes a frame 102, with an aperture 106, a suspensions system 104, unsafe UV-C emitters 110, as well as visible light LEDs 115. Additionally, 100B includes 'safe' UV-C emitters 120 in the range of 200-235 nm, preferably 222 nm or 233 nm are desired. These safe UV-C emitters 120 are positioned on the lower facing portion of the frame 102 and direct the safe UV-C emissions downward into the room and space being illuminated by the visible light LEDs. Additionally, 100B can be paired with one or more barrier sensors 130 that are configured to create a barrier, and preferably an invisible barrier, at or just below the frame 102. This is to ensure that if a living being breaches this barrier 170 the sensors can communicate with a controller 140 to shutoff the unsafe UV-C emitters 110. The sensors can be positioned on or separate from the frame 102, here they are shown as separate from the frame 102.

Figure 2:
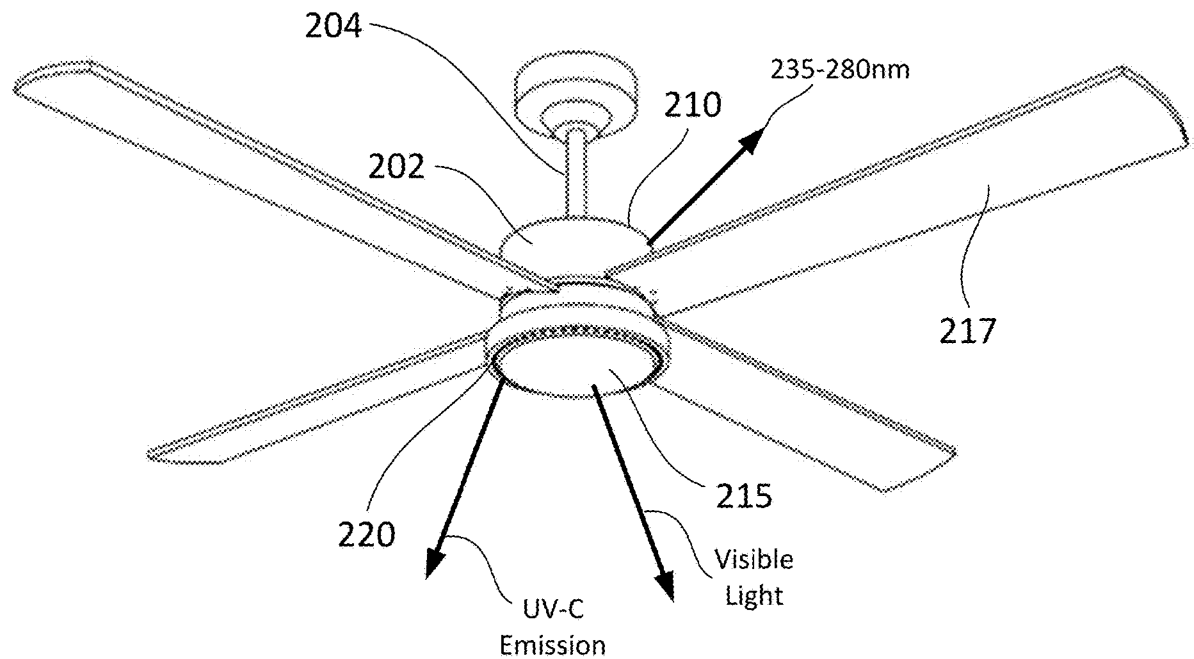
FIG. 2 is an illustration of another alternative air purifying light system with an integrated air circulating system.

FIG. 2 is an illustration of yet another alternative air purifying light system 200 with an integrated air circulating system. Similar to the other embodiments, system 200 includes a frame 202 that has an upper facing portion configured to mount 'unsafe' UV-C emitters 210, as well as a downward facing portion that is configured to mount visible light LEDs 215 as well as UV-C emitters 220. The 220 emitters could be either be in the unsafe 235-280 nm emitter range or in the safe 200-235 nm emitter range. In some variations both safe and unsafe ranges could be on the lower facing portion of the frame 202. The frame 202 is suspended from the ceiling using a suspension system 204. As noted, system includes an air circulating system that include one or more fan blades 217 to assist in circulating air into or out of the purification zone, which is the area disposed between the frame and the ceiling, wherewith the unsafe UV-C emitters direct their emissions. Although not shown in this embodiment, it is within the scope to further include downward facing safe UV-C emitters on the lower facing portion of frame 202. A sensing system, such as that shown in FIG. 1B could also be integrated with system 200.

Figure 3:
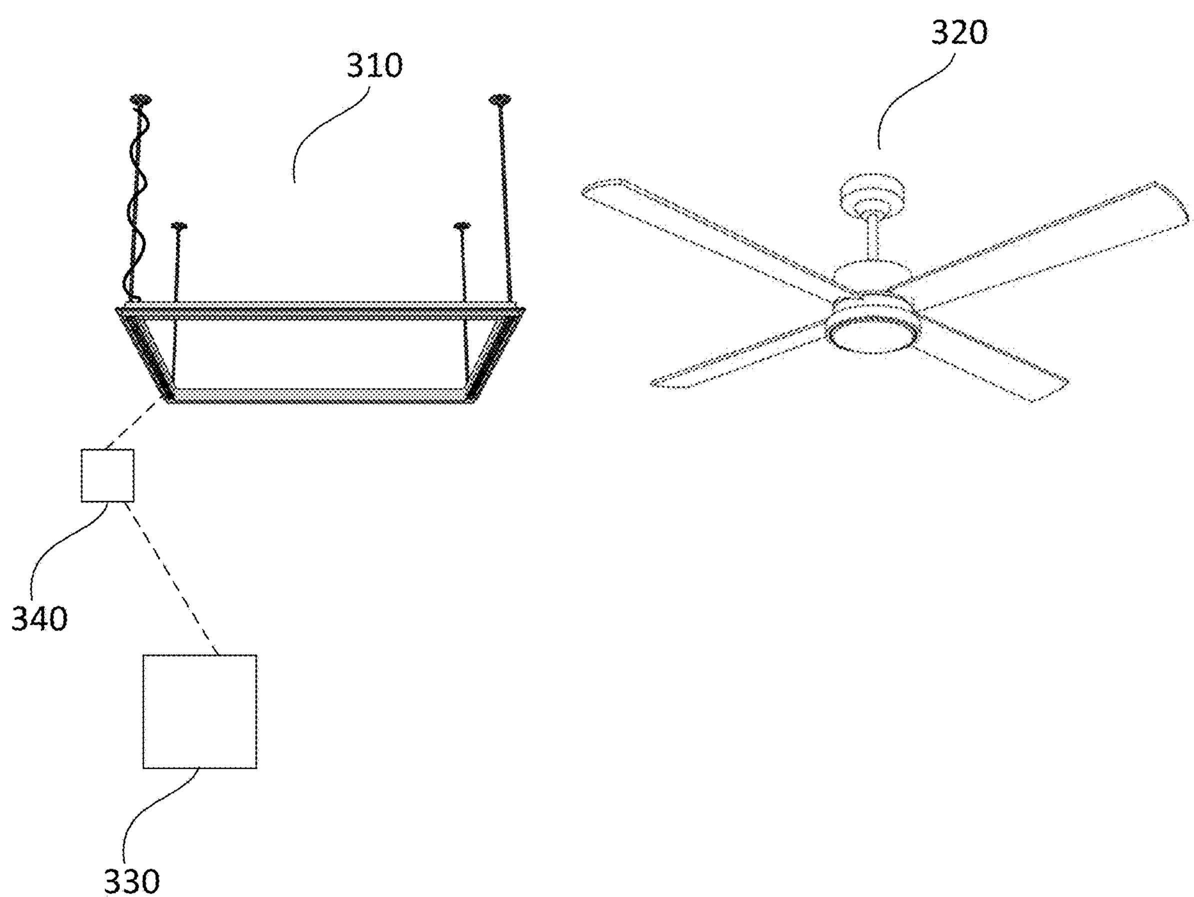
FIG. 3 is yet another alternative embodiment of an air purifying light system that includes an air circulating system and occupancy sensor system.

FIG. 3 is yet another alternative embodiment of an air purifying light system 300 that includes an air purifying light assembly 310, an air circulating system 320 and occupancy sensor system 340 that is in communication with a controller 340 that could be included with or separate from the assembly 310. One advantage of including an occupancy sensor is that unsafe UV-C emitters in the range of 235-280 nm could be positioned on the assembly 310 in a downward facing position, such as on the lower facing portion of the frame. These downward facing UV-C emitters would only operate when the occupancy sensor determines that no living beings are in the room or vicinity. The assembly 310 could also include unsafe UV-C emitters positioned above the frame of the assembly 310 that can operate while occupants are in the room below, thus creating an effective air purification system and lighting system.

If it is not already understood, by integrating these visible light and UV-C emitters into the systems described herein, it eliminates the need for extensive modifications to an HVAC system already present in a building, which substantially reduces installation and labor costs.

It should also be understood that smaller fans or circulating systems could be directly attached to or work in conjunction with for example systems 100A and 100B described above.

The suspension system 104/204 can be configured to suspend the frame 102/202 at least 1 foot below the ceiling, at least 2 feet below the ceiling and at least 4 feet below the ceiling. Thus, creating a volume or sanitization zone that is much larger in volume than traditional enclosed systems. This larger volume, as well as the positioning of such, is advantageous to simpler or even non-existent active air circulating systems. In other words, the sanitization zone can include the same perimeter and shape of the volume below the frame of the air purifying light system. This can be achieved with a single system having unsafe emitters positioned to emit to the entire space above the frame or provided by multiple systems, such as 100A or 100B positioned above the upper portion of a given room. No current sanitization system using UV-C emission matches the sanitization zone shape to that of the room it is sterilizing, which is another advantage of the system provided herein.

Of course, the present invention is not limited to the above features and advantages. Those of ordinary skill in the art will recognize additional features and advantages upon reading the following detailed description, and upon viewing the accompanying drawings.

Notably, modifications and other embodiments of the disclosed invention(s) will come to mind to one skilled in the art having the benefit of the teachings presented in the foregoing descriptions and the associated drawings. Therefore, it is to be understood that the invention(s) is/are not to be limited to the specific embodiments disclosed and that modifications and other embodiments are intended to be included within the scope of this disclosure. Although specific terms may be employed herein, they are used in a generic and descriptive sense only and not for purposes of limitation.

The invention claimed is:

1. An air purifying light system, comprising:

a frame having an upper facing portion and a lower facing portion;

a plurality of visible light emitting LEDs positioned on the lower facing portion of the frame, to direct visible light below; and a plurality of UV-C emitters positioned on the upward facing portion, which are configured to kill viruses and pathogens, thus sterilizing the air above the frame; and a second plurality of UV-C emitters positioned on the lower facing portion of the frame; and a room occupancy sensor, and a controller; and wherein the room occupancy sensor and controller are configured to control the second plurality of UV-C emitters positioned on the lower facing portion, based on the sensed occupancy in a room or area where the air purifying light system is installed by the room occupancy sensor independently of control of the plurality of UV-C emitters positioned on the upward facing portion.

2. The air purifying light system of claim 1 further comprising a suspension system, configured to suspend the frame from below the ceiling.

3. The air purifying light system of claim 2, wherein the suspension system is configured to suspend the frame at least 1 foot below the ceiling, at least 2 feet below the ceiling, and at least 4 feet below the ceiling.

4. The air purifying light system of claim 1 wherein the plurality of UV-C emitters positioned on the upward facing portion emit UV-C in the range of 235-280 nm.

5. The air purifying light system of claim 4 wherein the second plurality of UV-C emitters positioned on the lower facing portion emit UV-C in in the range of 200-235 nm.

6. The air purifying light system of claim 1 wherein the second plurality of UV-C emitters positioned on the lower facing portion emit UV-C in in the range of 200-235 nm.

7. The air purifying light system of claim 1, further including one or more sensors positioned to form an invisible barrier shield at the level of the frame, wherein the one or more sensors are in communication with a controller that once an object is detected that passes through or interrupts the barrier causes the controller to turn off the plurality of UV-C emitters on the upward facing portion of the frame.

8. The air purifying light system of claim 1, further including an air circulating system that causes air below the frame to circulate with air above the frame.

9. The air purifying light system of claim 8, wherein the air circulating system includes one or more ceiling fans.

10. The air purifying light system of claim 9, wherein the one or more ceiling fans are directly connected to the frame.

11. The air purifying light system of claim 1, wherein the upward facing UV-C emitters are either 254 nm, 270 nm or 272 nm wavelength emitters.

12. The air purifying light system of claim 1, wherein the frame is comprised of an outer perimeter and an inner perimeter, having an aperture formed about the inner perimeter.

13. The air purifying light system of claim 1, wherein the ceiling is devoid of any of material that can reflect greater than 5% of the light generated by the UV-C emitters in the range of 235-280 nm on the upward facing portion.

* * * * *